United States Patent [19]

Mitzner et al.

[11] Patent Number: 4,727,042

[45] Date of Patent: Feb. 23, 1988

[54] CALIBRATOR COMPOSITION AND METHOD OF PRODUCING AND USING SAME FOR VETERINARY APPLICATIONS

[75] Inventors: Barry T. Mitzner; Colin F. Aldersley, both of Miami, Fla.

[73] Assignee: Southeast Vetlab Inc., Miami, Fla.

[21] Appl. No.: 613,283

[22] Filed: May 24, 1984

[51] Int. Cl.$^4$ ............................................. G01N 31/00
[52] U.S. Cl. ........................................ 436/10; 436/18
[58] Field of Search ........................................ 436/8–16; 252/408.1; 422/61; 424/2; 435/2–4

[56] References Cited

U.S. PATENT DOCUMENTS

| | | | |
|---|---|---|---|
| 3,406,121 | 10/1968 | Jones | 23/230 B |
| 3,640,896 | 2/1972 | Casperis | 252/408 |
| 4,179,398 | 12/1979 | Hunt | 252/408 |
| 4,250,051 | 2/1981 | Armstrong | 252/408 |
| 4,264,470 | 4/1981 | Chastain et al. | 252/408 |
| 4,489,162 | 12/1984 | Hawkins et al. | 436/10 |

OTHER PUBLICATIONS

"The Status of Methods of Calibration in Hematology", *Amer. Society of Clinical Pathologists,* Gilmer et al., vol. 74, No. 4, pp. 600–605.

"Coulter Calibration Pak", by *Coulter Electronics Inc.,* 12-1977.

Clinical Diagnosis and Management-Laboratory Methods-Todd et al, John Bernard Henry, M.D. (W. B. Sanders Company), 1984.

The Technical Manual of the American Association of Blood Banks, Department of the Army, the Navy, the Air Force, Washington, DC, 7/29/77.

Hematology Calibrator-(American Dade Division), American Hospital Supply Corporation-product description.

Handout Distributed by Assignee (Southeast Vetlab, Inc.), at conference on Neurological Evaluation and Approaches to Therapy (May 19-20, 1979).

Copy of a letter dated Jun. 29, 1979, sent by President of Southeast Vetlab, Inc. to Dr. Jeanne George, University of Georgia.

*Primary Examiner*—Donald P. Walsh
*Assistant Examiner*—T. J. Wallen
*Attorney, Agent, or Firm*—Schwartz Jeffery Schwaab Mack Blumenthal & Evans

[57] ABSTRACT

Disclosed are a calibrator composition and method of producing and using the same in the analysis of blood of a particular species. From whole blood of the particular species, a solution is derived with which semi- and fully-automated particle counters can be calibrated for the particular species.

5 Claims, No Drawings

CALIBRATOR COMPOSITION AND METHOD OF PRODUCING AND USING SAME FOR VETERINARY APPLICATIONS

BACKGROUND OF THE INVENTION

The present invention relates to a method for calibrating fully and semi-automatic particle counters used in hemocytologic analysis to a specific species. The present invention further relates to compositions that can be employed in calibrating such counters so that the counters can be used in the accurate analysis of blood from different species.

It is well accepted in the medical field that a count of various cellular elements in blood can be correlated to certain disease states in humans. The use of hemocytometer counting chambers provides the ability manually to quantitate the cellular elements in a blood sample from a subject. Presently, there are also available fully- and semi-automated particle counters for use in making such blood analyses in human medicine, including counters manufactured by Coulter Electronics, Inc., of Hialeah, Fla. The wide use of counters in human blood analysis is evidenced by the development of human counter solutions and calibration procedures for such counters, which solutions are the subject of U.S. Pat. Nos. 4,250,051 (Armstrong) and 3,406,121 (Jones).

Fully automated counters are the rule in human medicine today. It is common medical diagnostic procedure to analyze and test the blood sample of a patient in order to make certain classic determinations with respect to the blood sample. This procedure is an acknowledged, important aid to a physician. The characteristic parameters monitored include red blood count (RBC), white blood count (WBC), hematocrit (HCT), hemoglobin (Hgb), mean corpuscular volume (MCV), mean corpuscular hemoglobin (MCH), and mean corpuscular hemoglobin concentration (MCHC). As noted above, Coulter Electronics, Inc. and other manufacturers sell several models of blood cell counting and analyzing instruments which are well-known in human medicine. Instruments are available which will accept a patient's blood sample and process the same sample automatically and continuously to provide one or more of the aforementioned parameters.

As disclosed by Armstrong, operation of an automatic counting instrument of the type commonly used for human blood analyses requires periodically confirming that the instrument's performance still conforms with the counting parameters internally pre-set when the instrument was placed in operation. This periodic confirmation of predetermined instrument values, which will hereinafter be called "standardization," is carried out by running a composition or "control" similar in nature to that of blood samples routinely encountered, through an instrument for which the counting parameters have previously been established, that is, through an instrument which has already been "calibrated." By evaluating the instrument's readings for the control against the control's known characteristic parameters, the user obtains a check on the continued precision of instrument in adhering to the pre-set calibration values.

Heretofore, the calibration values themselves were established by what Armstrong describes as "reference procedures." Routinely, specimens of fresh blood drawn from as many as 20 or more donors were divided into multiple aliquots and cycled through a particular instrument to obtain an average value and deviation standard for each characteristic parameter. Thereafter, the instrument was adjusted internally ("calibrated") so that the range of each counting parameter coincided with the "normal" range defined by the average and standard deviation of the corresponding characteristic parameter for the blood samples. Whether the instrument remained within these calibrated ranges had to be monitored regularly by the above-described standardization procedure.

While controls were available in the prior art for the latter procedure, a calibration method of like simplicity and general applicability was not available. In accordance with the present invention, however, there are provided an improved process for non-human blood analysis and a method of preparation of a calibrator solution of the particular species under examination for calibrating fully- and semi-automated particle counters. The inventors, Barry T. Mitzner, Doctor of Veterinary Medicine in the State of Florida, and Colin F. Aldersley, a licensed medical technologist within the State of Florida, have found that the use of human counter solutions and calibration procedures to analyze non-human blood can result in inaccurate counts by up to 30%. Also, conventional calibration procedures are impracticable for veterinary application, being too time consuming and prone to inaccuracies by virtue of the numerous dilutions they entail.

SUMMARY OF THE INVENTION

It is therefore an object of the present invention to provide a method for calibrating fully-and semi-automated particle counters so that blood samples from different species can be accurately analyzed using the same particle counter.

It is another object of the present invention to provide a composition that can be used to calibrate a particle counter so that the counter can then be used to count blood elements within a certain size range which is appropriate for the particular species being studied.

In accomplishing the foregoing objects, there has been provided according to the present invention a method of calibrating a blood analyzing apparatus which comprises a particle counter having a counter chamber of known volume, the method comprising the steps of (a) providing a calibrator solution produced by a process comprising the steps of (1) drawing at least one first sample of whole blood from each of a plurality of individuals of the same species, (2) fixing the dimensions of cellular components comprising each first sample, then (3) removing immunogenic factors from each of the first samples, and (4) after step (3), pooling all of the first samples to form a single second sample, the number of cellular components per unit volume of the second sample being determined; and (b) adjusting the threshold settings of the particle counter so that a reading obtained from the counter for an aliquot of the known volume derived from the second sample corresponds to the previously determined number of cellular components per unit volume of the second sample. In a preferred embodiment of the present invention, the aliquot derived from the second sample is introduced into the counting chamber of the counter apparatus without any preparatory dilution or other manipulation which might introduce error into the final measurements.

In further accomplishing the foregoing objects, there has also been provided, in accordance with the present invention, a kit comprising a plurality of separate calibrator solutions, each of the calibrator solutions being the product of a process comprising the steps of: (1) drawing at least one first sample of whole blood from each of a plurality of individuals of the same species, (2) fixing the dimensions of cellular components comprising each first sample, then (3) removing immunogenic factors from each of the first samples, (4) after step (3), pooling all of the first samples from the plurality of individuals to form a single second sample, and (5) determining the number of cellular components per unit volume of the second solution, each of the calibrator solutions having been produced from whole blood of a different species.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENT

In veterinary medicine, many different species must be treated. Unfortunately, cellular structure, composition, and size vary greatly among species. The present availability of human whole-blood controls only provides a reference for the other mammal, avian, or reptile cells in relationship to human cells; therefore, the use of counting instruments which have been calibrated against human control solutions, a common practice in veterinary laboratories now, introduces significant inaccuracies into diagnoses based on the instrument readings. Due in part to these inaccuracies, the use of semi-automated and automated instruments in veterinary practice has lagged behind the use in human medicine.

Thus, while semi-automated and automated counting of blood components is the rule in human medicine, it is only within the last five to ten years that counting instruments and their allied technology have been applied in the veterinary field. From a purely mechanical and theoretical standpoint, the instruments themselves are easily applicable to veterinary practice. But with the expansion of veterinary practice beyond the common domestic species (e.g., horse, cow, dog, cat), the effectiveness of such counting instrument in yielding accurate readings has been reduced in a manner which is not apparent to those using the instruments in veterinary applications. This reduction is not by fault of the instrumentation, but rather by fault of the allied calibrating methodology, which is based entirely on human clinical practice.

More specifically, a typical counting instrument is designed so that a cellular element passing through an aperture associated with an electrical field in the instrument's counting chamber creates a change in the impedance across the aperture which is proportional to the volumetric displacement of the cellular element. This impedance change is converted into an electrical pulse which is recorded as a count if the size of the pulse is within a range corresponding to pre-set threshold values of the instrument. Thus, particles above or below a pre-established size range are excluded.

To further demonstrate how the establishing of the particle size range affects a counter's readings, reference is made to the following estimates of the mean corpuscular volume (MCV) for cats and humans, respectively, the reported values reflecting a difference in the relative dimensions of red blood cells in the two species:

| Species | Mean Corpuscular Volume (Cu/u) (Established by Manual Methods) |
| --- | --- |
| Feline | 39–55 |
| Human | |
| Male | 80–94 |
| Female | 81–99 |

From the preceding data, it can be appreciated that only feline blood elements having dimensions that overlap into the human range will be counted by an instrument calibrated using a human control solution. By lowering the threshold settings of the instrument to include all feline cells in the count, rather than just those with dimensions in the human range, an increase in the total cell count can be expected and more accurate blood analysis obtained.

It is also evident that cell size and total cell count will normally be closely linked. Demonstrable differences in the respective dimensions of animal and human cellular elements, such as red blood cells, therefore translate into obvious differences in total cell count. The present invention permits the ordinary practitioner to accommodate species-specific differences in the size of blood elements by calibrating a standard counter to take actual size ranges for blood elements of different species into account, thereby opening the possibility of borrowing from the body of published knowledge concerned with human clinical interpretation of hematologic parameters.

A blood analysis in accordance with the present invention begins with the drawing of whole blood samples from a number of individuals of the species to be tested. Each blood sample is then washed repeatedly with an isotonic solution to remove all plasma proteins, and is placed in a buffered isotonic solution. An aldehyde is slowly added while simultaneous gentle agitation is provided. The aldehyde treatment will stabilize or "fix" the cells' dimensions. After the fixed cells are rinsed of the aldehyde by washing them again in a buffered isotonic solution, they are concentrated in a centrifuge and rewashed. The steps of washing and centrifuging can be repeated several times to insure removal of all of the aldehyde solution.

After the aldehyde is removed, all of the blood samples are pooled and an isotonic diluent, such as physiologic saline, is added to ensure that the tonicity of the pooled volume approximates that of blood plasma, thereby minimizing any deformation of blood elements in the final solution. From the latter, an aliquot is derived having a volume equal to that of the counting chamber of the counter to be used and the number of blood elements (such as red blood cells) therein per cubic millimeter is determined, e.g., manually. The test aliquot (or a second aliquot of equal volume) is then placed in the counting chamber, and the threshold values of the counter are adjusted so that the resulting reading corresponds to the cell count previously obtained.

Thus calibrated, the counter can be used to obtain accurate counts for blood from individual subjects of the particular species. If another species' blood is to be analyzed, the counter can be readily calibrated to new threshold values, using a calibrating solution prepared, as described above, from blood of the other species. In this fashion, a single counter can be used effectively in the analysis of blood samples from the wide variety of species commonly encountered in veterinary practice. For example, a given veterinary laboratory could be provided, in accordance with the present invention, with a series of calibrating solutions, each solution being used as the need arose to calibrate the laboratory's counter for a different species, following the above-described procedure.

What is claimed is:

1. A method of calibrating a blood analyzing apparatus which comprises a particle counter having a counter chamber of known volume, said method comprising the steps of
   (a) providing at least a first calibrator solution and a second calibrator solution, each of the calibrator solutions (i) comprising elements of fixed dimensions that correspond to those of blood components of a first and a second species, respectively, and (ii) being the product of a process comprising the steps of
      (1) drawing at least one first sample of whole blood from each of a plurality of individuals of the same species,
      (2) stabilizing the dimensions of cellular components comprising each first sample, then
      (3) removing immunogenic factors from each of said first samples, and
      (4) after step (3), pooling all of said first samples from said plurality of individuals to form a single pooled sample, having a known number of cellular components per unit volume of said pooled sample;
   (b) adjusting the threshold settings of said particle counter so that a reading obtained from said counter for an aliquot of said known volume derived from said first calibrator solution corresponds to a known number of cellular components per unit volume of a pooled sample prepared using first samples from said first species; and thereafter
   (c) readjusting the threshold settings of said particle counter so that a reading obtained from said counter for an aliquot of said known volume derived from said second calibrator solution corresponds to a known number of cellular components per unit volume of a pooled sample produced using first samples from said second species.

2. A method according to claim 1, wherein said fixing comprises the step of adding to each of said first samples a predetermined amount of an aldehyde to stabilize the dimensions of said cellular components.

3. A method according to claim 1, wherein said cellular components consist essentially of red blood cells.

4. A method according to claim 1, wherein said step (b) comprises introducing said aliquot into said counter chamber without a preparatory dilution of said aliquot.

5. A method according to claim 1, wherein said removing step (3) comprises washing each of said first samples in an isotonic solution.

* * * * *